US012084459B2

(12) United States Patent
Nir et al.

(10) Patent No.: US 12,084,459 B2
(45) Date of Patent: Sep. 10, 2024

(54) 2-(4-{1-[6-(4-ISOPROPYL-PHENYL)-IMIDA-ZO[2,1-B][1,3,4]THIADIAZOL-2-YL]-PIPER-IDIN-4-YLMETHYL}-PIPERAZIN-1-YL)-ETHANOL AND USE THEREOF (71) Applicant: Urifer Ltd., Ra'anana (IL)

(72) Inventors: Uri Nir, Moshav Gamzo (IL); Sally Shpungin, Ramat-Gan (IL)

(73) Assignee: Urifer Ltd., Ra'anana (IL)

( * ) Notice: Subject to any disclaimer, the term of this patent is extended or adjusted under 35 U.S.C. 154(b) by 606 days.

(21) Appl. No.: 17/212,845

(22) Filed: Mar. 25, 2021

(65) Prior Publication Data

US 2021/0309672 A1 Oct. 7, 2021

(30) Foreign Application Priority Data

Apr. 1, 2020 (IL) .......................................... 273739

(51) Int. Cl.
C07D 513/04 (2006.01)
A61P 35/04 (2006.01)
(52) U.S. Cl.
CPC ............ *C07D 513/04* (2013.01); *A61P 35/04* (2018.01)
(58) Field of Classification Search
CPC .............................. C07D 513/04; A61P 35/04
See application file for complete search history.

(56) References Cited

U.S. PATENT DOCUMENTS

| 2005/0063973 A1 | 3/2005 | Nir et al. |
| 2013/0072448 A1 | 3/2013 | Nir et al. |
| 2018/0186815 A1 | 7/2018 | Nir et al. |

FOREIGN PATENT DOCUMENTS

| EP | 2401283 B1 | 8/2014 |
| WO | 2010097798 A1 | 9/2010 |
| WO | 2016135733 A1 | 9/2016 |

OTHER PUBLICATIONS

Allard, Pierre, et al. "Links Between Fer Tyrosine Kinase Expression Levels and Prostate Cell Proliferation." Molecular and Cellular Endocrinology, vol. 159, 2000, pp. 63-77., 2000, 63-77.
Berridge, Michael V., et al. "Tetrazolium Dyes as Tools in Cell Biology: New Insights into Their Cellular Reduction." Biotechnology Annual Review, 2005, pp. 127-152., doi:10.1016/s1387-2656(05)11004-7., 2005, 127-152.
Craig, Andrew W., et al. "Mice Devoid of Fer Protein-Tyrosine Kinase Activity Are Viable and Fertile but Display Reduced Cortactin Phosphorylation." Molecular and Cellular Biology, vol. 21, No. 2, 2001, pp. 603-613., doi:10.1128/mcb.21.2.603-613.2001., 2001, 603-613.
Craig, Andrew W., and Peter A. Greer. "Fer Kinase Is Required for Sustained p38 Kinase Activation and Maximal Chemotaxis of Activated Mast Cells." Molecular and Cellular Biology, vol. 22, No. 18, 2002, pp. 6363-6374., doi:10.1128/mcb.22.18.6363-6374.2002.
Elkis, Yoav, et al. "A Novel Fer/FerT Targeting Compound Selectively Evokes Metabolic Stress and Necrotic Death in Malignant Cells." Nature Communications, vol. 8, No. 1, Oct. 16, 2017, pp. 1-17., doi:10.1038/s41467-017-00832-w., Oct. 16, 2017, 1-17.
Greer, Peter. "Closing in on the Biological Functions of Fps/Fes and Fer." Nature Reviews Molecular Cell Biology, vol. 3, No. 4, Apr. 2002, pp. 278-289., doi:10.1038/nrm783., Apr. 2002, 278-289.
Hao, Qian-Lin, et al. Isolation and Sequence Analysis of a Novel Human Tyrosine Kinase Gene, vol. 9, No. 4, Apr. 1989, pp. 1587-1593., doi:10.1128/eissn.1098-5549., Apr. 4, 1989, 1587-1593.
Kim, Leung, and Tai Wai Wong. "Growth Factor-Dependent Phosphorylation of the Actin-Binding Protein Cortactin Is Mediated by the Cytoplasmic Tyrosine Kinase FER." Journal of Biological Chemistry, vol. 273, No. 36, Sep. 4, 1998, pp. 23542-23548., Sep. 4, 1998, 23542-23548.
Luo, Xin, et al. "Clinicopathological Significances of Feline Sarcoma-Related Protein and β2-Adrenoceptor Expression in Pancreatic Ductal Adenocarcinomas." International Journal of Clinical and Experimental Pathology, vol. 12, No. 9, Sep. 15, 2019,, Sep. 15, 2019, 3390-3398.
Orlovsky, Kira, et al. "N-Terminal Sequences Direct the Autophosphorylation States of the FER Tyrosine Kinases in Vivo." Biochemistry, vol. 39, No. 36, Aug. 12, 2000, pp. 11084-11091., doi:10.1021/bi0005153., Aug. 12, 2000, 11084-11091.
Pasder, O, et al. "Downregulation of Fer Induces PP1 Activation and Cell-Cycle Arrest in Malignant Cells." Oncogene, vol. 25, No. 30, May 29, 2006, pp. 4194-4206., doi:10.1038/sj.onc.1209695., May 29, 2006, 4194-4206.
Pasder, P., et al. "FER as a Novel Intervening Target for Cancer Therapy." Drugs of the Future, vol. 32, No. 1, 2007, pp. 61-70., doi:10.1358/dof.2007.032.01.1065737., 2007, 61-70.
Penhallow, Robert C., et al. "Temporal Activation of Nontransmembrane Protein-Tyrosine Kinases Following Mast Cell FcεRI Engagement." Journal of Biological Chemistry, vol. 270, No. 40, Oct. 6, 1995, pp. 23362-23365., doi:10.1074/jbc.270.40.23362., Oct. 6, 1995, 23362-23365.
Yaffe, Etai, et al. "Oncogenic Properties of a Spermatogenic Meiotic Variant of Fer Kinase Expressed in Somatic Cells." Cancer Research, vol. 74, No. 22, Sep. 18, 2014, pp. 6474-6485., doi:10.1158/0008-5472.can-14-0058., Sep. 18, 2014, 6474-6485.

*Primary Examiner* — Shobha Kantamneni
(74) *Attorney, Agent, or Firm* — Dorsey & Whitney LLP

(57) ABSTRACT

The present disclosure is directed to a compound of formula (I) (E266) and its acceptable pharmaceutical salts, to pharmaceutical compositions comprising the compound and its use in the manufacture of medicaments for treating diseases.

5 Claims, 7 Drawing Sheets

Figure 2: normal epithelial cells are not effected by either one of Z522-251 and compound of formula (I)

Figure 3: Activity of Z522-251 and compound of formula (I) in killing metastatic colon cancer SW620 cells Figure 4: Activity of Z522-251 and compound of formula (I) in killing metastatic pancreatic ductal adenocarcinoma Su.86.86 cancer cells Figure 5: Activity of Z522-251 and compound of formula (I) in killing ll metastatic Triple negative MDA-MB-231 Breast cancer cells Figure 6: Activity of Z522-251 and compound of formula (I) in killing metastatic adenocarcinoma PC3 prostate Cancer cells Figure 7: H358 (Metastatic NSCLC) Xenografts –subcutaneously injected to "nude" mice- compounds were daily injected IP, 25mg/kg in 1% Tween 80 (Polysorbate 80)

2-(4-{1-[6-(4-ISOPROPYL-PHENYL)-IMIDAZO[2,1-B][1,3,4]THIADIAZOL-2-YL]-PIPERIDIN-4-YLMETHYL}-PIPERAZIN-1-YL)-ETHANOL AND USE THEREOF

FIELD OF THE INVENTION

This invention relates to an imidazo[2,1-b][1,3,4]thiadiazole derivative, process for its manufacture and its use in medicaments.

BACKGROUND OF THE INVENTION

The following references are considered to be relevant for an understanding of the invention.

REFERENCES

Allard P, Zoubeidi A, Nguyen L T, Tessier S, Tanguay S, Chevrette M, Aprikian A and Chevalier S. (2000). *Mol. Cell. Endocrinol.*, 159, 63-77.

Berridge, M. V., Herst, P. M., and Tan, A. S. (2005). Tetrazolium dyes as tools in cell biology: new insights into their cellular reduction. Biotechnol. Annu. Rev. 11, 127-152]

Craig A W and Greer P A. (2002). *Mol. Cell. Biol.*, 22, 6363-6374.

Craig A W, Zirngibl R, Williams K, Cole L A and Greer P A. (2001). *Mol. Cell. Biol.*, 21, 603-613.

Greer P. (2002). *Nat. Rev. Mol. Cell Biol.*, 3, 278-289.

Hao Q-L, Heisterkamp N and Groffen J. (1989). *Mol. Cell. Biol.*, 9, 1587-1593.

Kim L and Wong T W. (1998). *J. Biol. Chem.*, 273, 23542-23548.

Orlovsky K, Ben-Dor I, Priel-Halachmi S, Malovany H and Nir U. (2000). *Biochemistry*, 39, 11084-11091.

Penhallow R C, Class K, Sonoda H, Bolen J B and Rowley R B. (1995). *J. Biol. Chem.*, 270, 23362-23365.

Pasder, O., Shpungin, S., Salem, Y., Makovsky, A., Vilchick, S., Michaeli, S., Malovani, H. and Nir, U. (2006) *Oncogene*, 25, 4194-4206.

Pasder, O., Salem, Y., Yaffe, E., Shpungin, S. and Nir, U. (2007) *Drugs of the Future*, 32, 61-70.

Yaffe, E., Hikri, E., Elkis, Y., Cohen, O., Segal, A., Makovski, A., Varvak, A., Shpungin, S., and Nir, U. (2014) Oncogenic properties of a spermatogenic meiotic variant of fer kinase expressed in somatic cells. *Cancer Res.* 74, 6474-6485

Elkis, Y., Cohen, M., Yaffe, E., Satmary-Tusk, S., Feldman, T., Hikri, E., Nyska, A., Feiglin, A., Ofran, Y., Shpungin, S., and Nir, U. (2017) A novel Fer/FerT targeting compound selectively evokes metabolic stress and necrotic death in malignant cells. *Nat. Commun.* 8, 940

Luo, X., Yang, Z., Liu, X., Liu, Z., Mio, X., Li, D., Zou, Q., and Yuan, Y. (2019) Clinicopathological significances of Felinesarcoma-related protein and β2-adrenoceptorexpression in pancreatic ductal adenocarcinomas. Int J Clin Exp Pathol 2019; 12(9):3390-3398

Fer is an intracellular tyrosine kinase that resides in both the cytoplasm and nucleus of mammalian cells and is activated by growth factors such as EGF and PDGF in fibroblastic cells (Kim and Wong, 1998), and by occupation of the Fcγ receptor in mast cells (Penhallow et al., 1995). Although present in a wide variety of tissues and cells, the functional role of Fer has been elucidated mainly in cells which carry out innate immune responses (Craig and Greer, 2002; Greer, 2002). Mice devoid of an active Fer develop normally and the proliferation of fibroblasts derived from these mice is not impaired in vitro (Craig et al., 2001).

Fer was detected in all human malignant cell lines analyzed (Hao et al., 1989; Orlovsky et al., 2000) and its levels in malignant prostate (Allard et al., 2000), metastatic pancreatic and Triple negative breast cancer tumors (Luo et al. 2019), are significantly higher than those detected in normal cells. Furthermore, down-regulation of Fer impaired the proliferation of prostate and breast carcinoma cells (Pasder et al., 2006) and abolished the ability of prostate carcinoma PC3 cells to form colonies in soft agar (Allard et al., 2000). U.S. patent application Ser. No. 10/486,101 having Publication Number 20050063973 discloses short interfering RNA (siRNA) molecules directed to sequences of the fer gene. These siRNA molecules were found to inhibit the growth of PC3 cells and to arrest tumor growth in an animal model (Pasder et al., 2007).

EP 2401283 discloses imidazo[2,1-b][1,3,4]thiadiazole derivatives, processes for their manufacture and their use in medicaments.

SUMMARY OF THE INVENTION

In its first aspect the present invention relates to a compound of formula (I) (E266) or pharmaceutical salts thereof:

(I)

The invention is further directed to pharmaceutical compositions comprising the compound of formula (I) and its pharmaceutical acceptable salts.

The invention is further directed to the compound of formula (I) or its pharmaceutical acceptable salts for use in therapy.

The invention is further directed to the compound of formula (I)) or its pharmaceutical acceptable salts for use as a medicament for treating diseases and disorders.

The invention is further directed to the compound of formula (I) or its pharmaceutical acceptable salts for use in treating cancer.

The invention is further directed to the compound of formula (I) or its pharmaceutical acceptable salts for use for used in treating colon, pancreatic and breast cancers.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

The present invention is directed to a compound of formula (I) (E266) and its acceptable pharmaceutical salts, to pharmaceutical compositions comprising the compound and its use in the manufacture of medicaments for treating diseases. In particular, the compound may be used for treating cancer, such as colon, pancreatic and breast cancers. Acceptable pharmaceutical salts are selected from suitable pharmaceutically acceptable salts of the compounds of the invention include acid addition salts formed with pharmaceutically acceptable organic or inorganic acids, for example hydrochlorides, hydrobromides, sulphates, alkyl- or arylsulphonates (e. g. methanesulphonates or p-toluenesulphonates), phosphates, acetates, citrates, succinates, tartrates, trifluoroacetates, lactates, fumarates, malates and maleates. In particular tartare salt.

Figure 1:
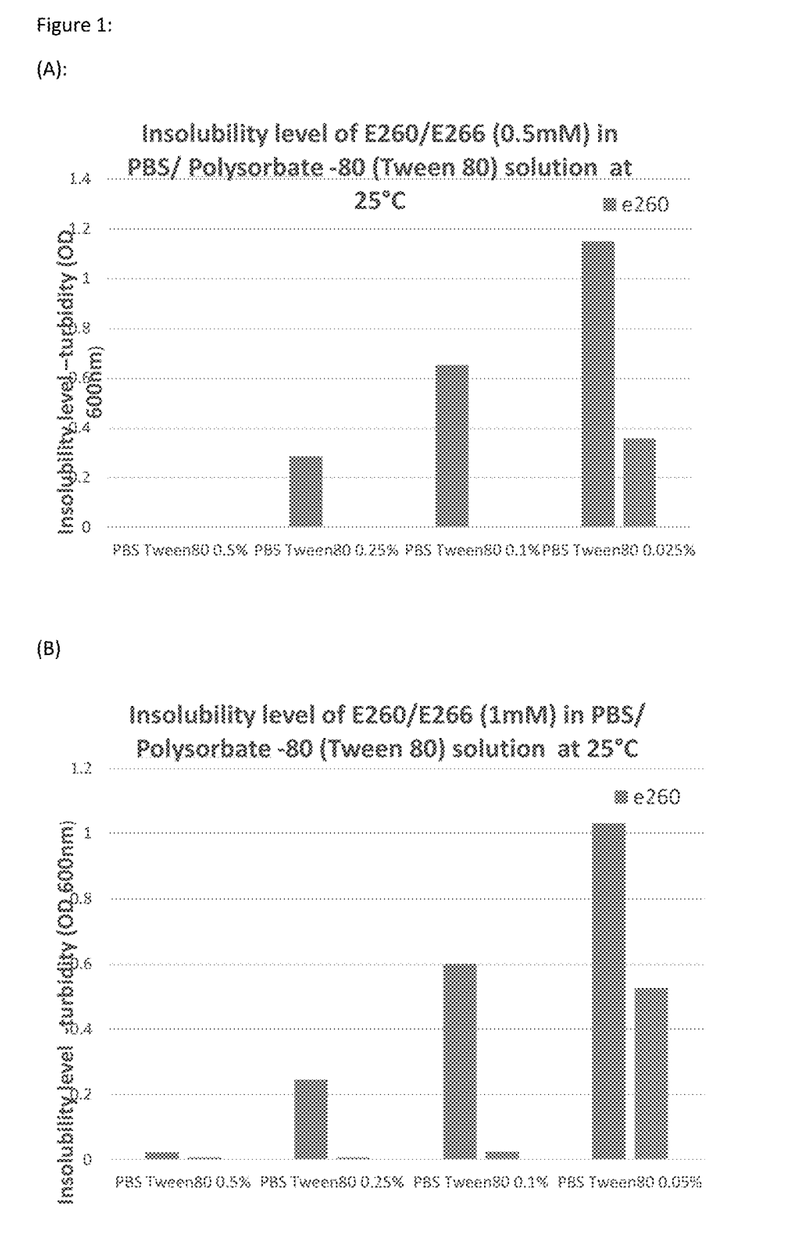
FIG. 1 shows (A) insolubility level of Z522-251 (E260; EP 2401283)/compound of formula (I) (E266) (0.5 mM) in PBS/Polysorbate-80 (Tween 80) solution at 25° C.; and (B) insolubility level of Z522-251 (E260)/compound of formula (I) (E266) (1 mM) in PBS/Polysorbate-80 (Tween 80) solution at 25° C.
Figure 2:
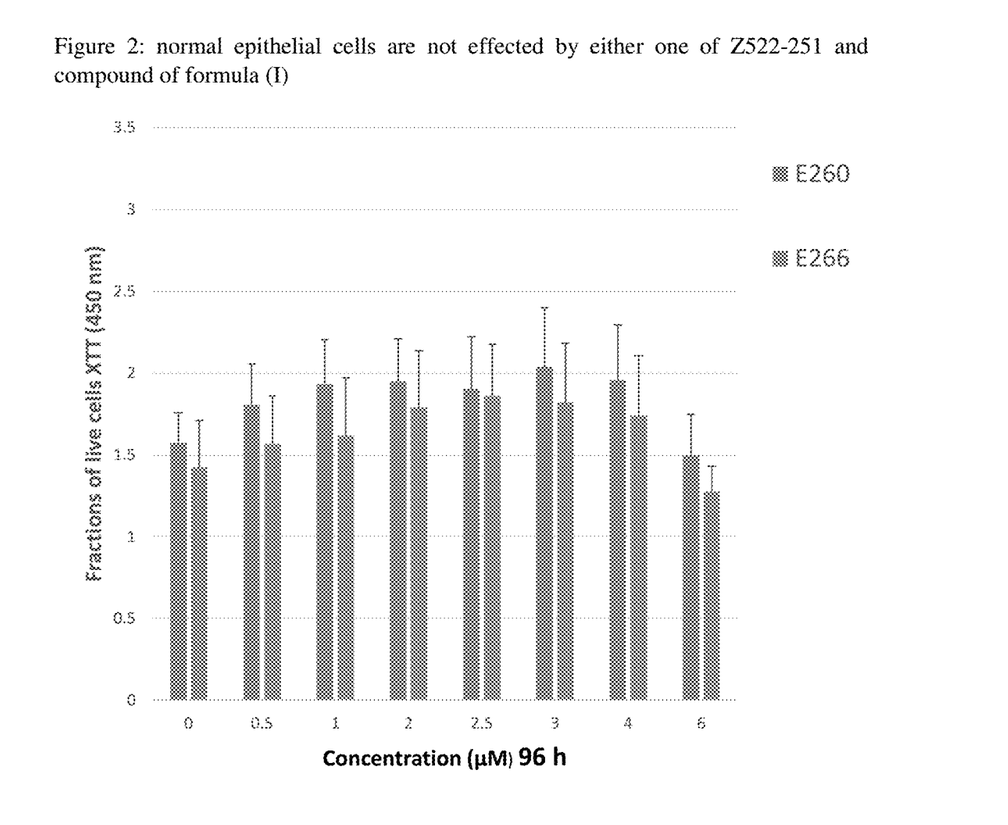
FIG. 2 shows that both compound of formula (I) (E266) and compound Z522-251 (E260) have no effect on normal Epithelial cells.

The present invention demonstrates an enhanced improvement in the solubility of previously known compounds. The compound of the present application demonstrates an improved solubility compared to the compound Z522-251 (E260) (EP 2401283):

The improved solubility of the compound of the present invention is demonstrated in FIGS. 1(A) and 1(B) where previously described compound Z522-251 is indeed insoluble. Compound (I) (E266) is soluble to a certain extent thus enabling to use smaller amounts of the active compound for achieving a therapeutically effect. The compound has no activity on healthy epithelial cells as demonstrated in FIG. 2. The compound is not toxic as demonstrated in the following Tables 1 (male mice), II (female mice) providing initial weight and body weight change (% wt/wt). Compound (I) was dissolved in 20% hydroxypropylcyclodextrane and the volume of administration (IP) was 10 ml/kg.

TABLE I

| | 1 | 2 | 3 | 4 | 5 | 6 | 7 | 8 |
|---|---|---|---|---|---|---|---|---|
| | | | | Day (date) | | | | |
| | | | | Dose (mg/kg) | | | | |
| | 16.9.2019 | 17.9.2019 | 18.9.2019 | 19.9.2019 | 20.9.2019 | 21.9.2019 | 22.9.2019 | 23.9.2019 |
| 400 | 40.3 | 40 | 41.3 | 40.8 | 39.6 | 40.4 | 40.5 | 40.7 |
| Change | 0 | −.07% | 2.5% | 1.2% | −1.7% | 0.2% | 0.5% | 1.0% |
| 200 | 37.8 | 38.1 | 38.2 | 38.3 | 37.6 | 38 | 39.2 | 39.7 |
| Change | 0 | 0.8% | 1.1% | 1.3% | −0.5% | 0.5% | 3.7% | 5.0% |
| 100 | 37.4 | 38.2 | 38 | 37.3 | 37.9 | 37.5 | 37.4 | 37.5 |
| Change | 0 | 2.1% | 1.6% | −0.3% | 1.3% | 0.3% | 0.0% | 0.3% |
| 0 | 40.3 | 39.9 | 40.1 | 39.8 | 40.4 | 39.9 | 40.2 | 40.4 |
| Change | 0 | −1.0% | −0.5% | −1.2% | 0.2% | −1.0% | 0.2% | 0.2% |
| | 9 | 10 | 11 | 12 | 13 | 14 | 15 | |
| | | | | Day (date) | | | | |
| | | | | Dose (mg/kg) | | | | |
| | 24.9.2019 | 25.9.2019 | 26.9.2019 | 27.9.2019 | 28.9.2019 | 29.9.2019 | 30.9.2019 | |
| 400 | 39.4 | 40 | 39.7 | 40.1 | 40.1 | 40.2 | 39.3 | |
| Change | −2.2% | −0.7% | −1.5% | −0.5% | −0.5% | −0.2% | −2.5% | |
| 200 | 38 | 37.9 | 38.2 | 38.7 | 37.9 | 38.8 | 37.6 | |
| Change | 0.5% | 0.3% | 1.1% | 2.4% | 0.3% | 2.6% | −0.5% | |

TABLE I-continued

|  | | | | | | | |
|---|---|---|---|---|---|---|---|
| 100 | 36.8 | 37.2 | 37.3 | 37.3 | 37.7 | 38.1 | 36.6 |
| Change | −1.6% | −0.5% | −0.3% | −0.3% | 0.8% | 1.9% | −2.1% |
| 0 | 39.3 | 40 | 39.9 | 40 | 40.4 | 40.9 | 40.3 |
| Change | −2.5% | −0.7% | −1.0% | −0.7% | 0.2% | 1.5% | 0.0% |

TABLE II

| | Day (date) | | | | | | | |
|---|---|---|---|---|---|---|---|---|
| | 1 | 2 | 3 | 4 | 5 | 6 | 7 | 8 |
| Dose (mg/kg) | | | | | | | | |
| | 16.9.2019 | 17.9.2019 | 18.9.2019 | 19.9.2019 | 20.9.2019 | 21.9.2019 | 22.9.2019 | 23.9.2019 |
| 400 | 31.1 | 30.5 | 29.6 | 28.6 | 28.4 | 28.5 | 28.4 | 28.7 |
| Change | 0 | −1.9% | −4.8% | −8.0% | −8.7% | −8.4% | −8.7% | −7.7% |
| 200 | 31.5 | 30.5 | 30.8 | 30.6 | 30.6 | 30.9 | 31 | 31.1 |
| Change | 0 | −3.2% | −2.2% | −2.9% | −2.9% | −1.9% | −1.6% | −1.3% |
| 100 | 36.1 | 35.7 | 36.1 | 35.2 | 34.0 | 33.9 | 34 | 33.6 |
| Change | 0 | −1.1% | 0.0% | −2.5% | −5.8% | −6.1% | −5.8% | −6.9% |
| 0 | 26.3 | 26.3 | 26.3 | 26.6 | 26.7 | 26.9 | 27.3 | 27.9 |
| Change | 0 | 0.0% | 0.0% | 1.1% | 1.5% | 2.3% | 3.3% | 6.1% |

| | Day (date) | | | | | | |
|---|---|---|---|---|---|---|---|
| | 9 | 10 | 11 | 12 | 13 | 14 | 15 |
| Dose (mg/kg) | | | | | | | |
| | 24.9.2019 | 25.9.2019 | 26.9.2019 | 27.9.2019 | 28.9.2019 | 29.9.2019 | 30.9.2019 |
| 400 | 29 | 29.3 | 29 | 29.4 | 29.8 | 29.8 | 29.2 |
| Change | −6.8% | −5.8% | −6.8% | −5.5% | −4.2% | 4.2% | −6.1% |
| 200 | 30.6 | 31.2 | 29.9 | 30.6 | 30.6 | 30.8 | 30.5 |
| Change | −2.9% | −1.0% | −5.1% | −2.9% | −2.9% | −2.2% | −3.2% |
| 100 | 32.4 | 33.5 | 32.6 | 33.4 | 32.8 | 32.2 | 32.4 |
| Change | −10.2% | −7.2% | −9.7% | −7.5% | −9.1% | −10.8% | −10.2% |
| 0 | 27.2 | 27.1 | 25.9 | 26.6 | 27.3 | 27.8 | 27.3 |
| Change | 3.4% | 3.0% | −1.5% | 1.1% | 3.8% | 5.7% | 3.8% |

It should be commented that a decrease in locomotor and piloererection right after administration were observed, these were reversible and full recovery was observed.

The pharmaceutical compositions according to the present invention may be in a solid form of capsules, tablets; may be in a form suitable for topical administration as ointments, creams, lotions, gels. Alternatively, it may be in the form of drops, syrups, suspensions, injectable powders or liquid in ampoules.

When present in a liquid form, the active component according to the present invention is dissolved in a solvent or mixture of solvents that are allowed for in vivo use (GRAS). In particular, DMSO, Cyclodextrins, such as α-Cyclodextrin, 2-hydroxypropyl-β-cyclodextrin, 3-hydroxypropyl-β-cyclodextrin, 4-Sulfo-butyl-cyclodextrin solutol, cremophor or polysorbate 80 (Tween 80), were used. The compositions may comprise carbohydrates such as, lactose, dextrose, sucrose, trehalose, dextrates.

EXPERIMENTAL

Chemical Synthesis

Compound of formula (I) (designated as Z522-266) was prepared according to Scheme 1:

Scheme 1

Biological Activity
Liquid Formulations

The compound (I), as tartarate salt was dissolved in 0.5% Tween-80 to affect the viability of several cell lines as follows. The results for the viability of the treated cells are given in FIGS. 3-6.

In Vivo Activity

The effect of the compound (I) (E266) on the growth profile of cancer cells which express Fer was tested. The cells that were tested were: the metastatic colon cancer cell line—SW620, the metastatic pancreatic ductal-adenocarcinoma SU.86.86 cancer cell-line—SU.86.86, the metastatic Triple Negative breast cancer cell line—MDA-MB-231, and the metastatic prostate cancer cell-line—PC3. The effect of the compound (I) (E266) on FS11 cells, a non malignant fibroblastic cell line, was also studied.

Examples 1-4

Figure 3:
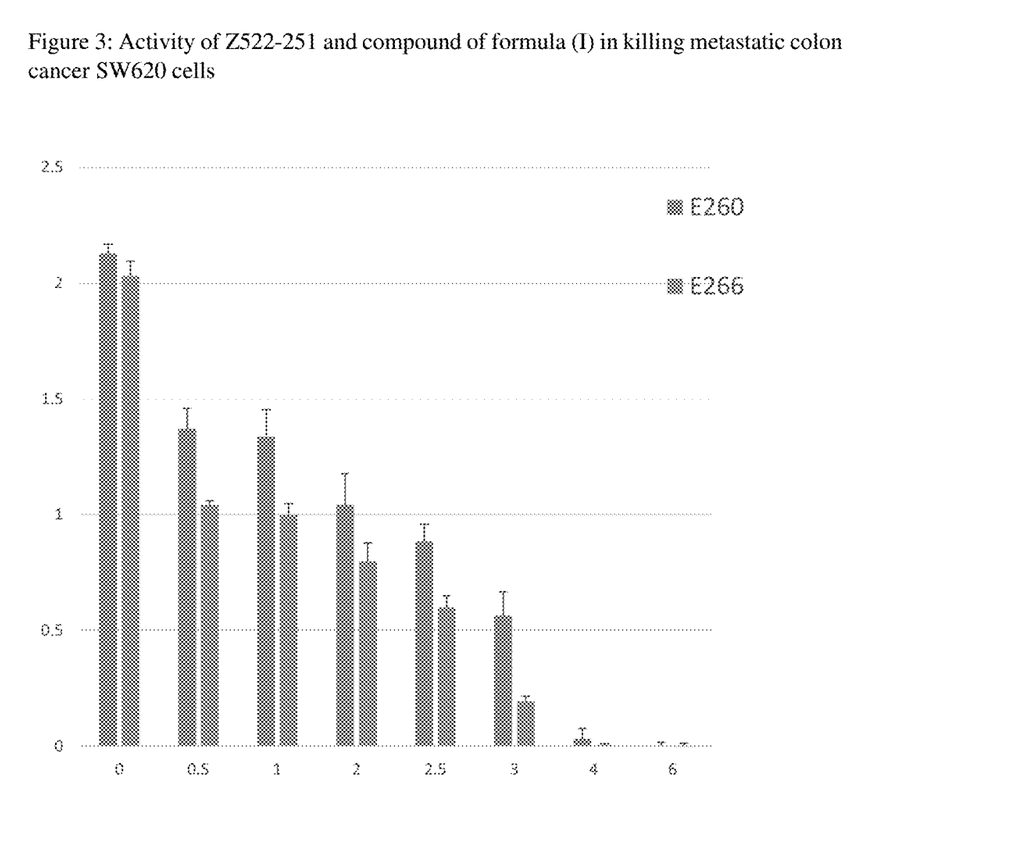
FIG. 3 shows the comparisons of the effect of compound of formula (I) (E266) and of compound Z522-251 (E260) on killing metastatic colon cancer SW620 cells.
Figure 4:
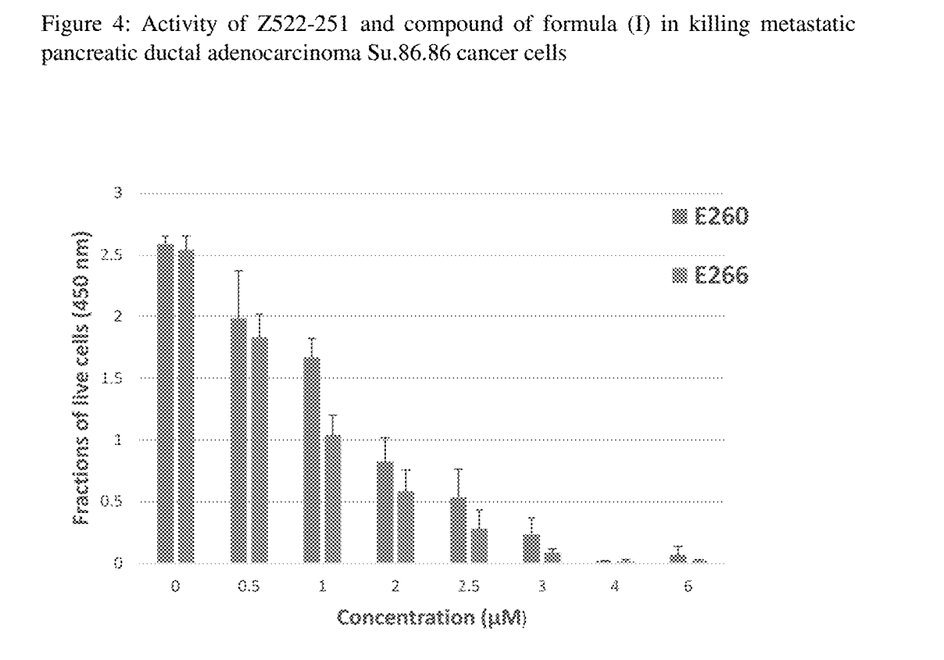
FIG. 4 shows the comparisons of the effect of compound of formula (I) (E266) and of compound Z522-251 (E260) on killing metastatic pancreatic ductal adenocarcinoma Su.86.86 cancer cells.
Figure 5:
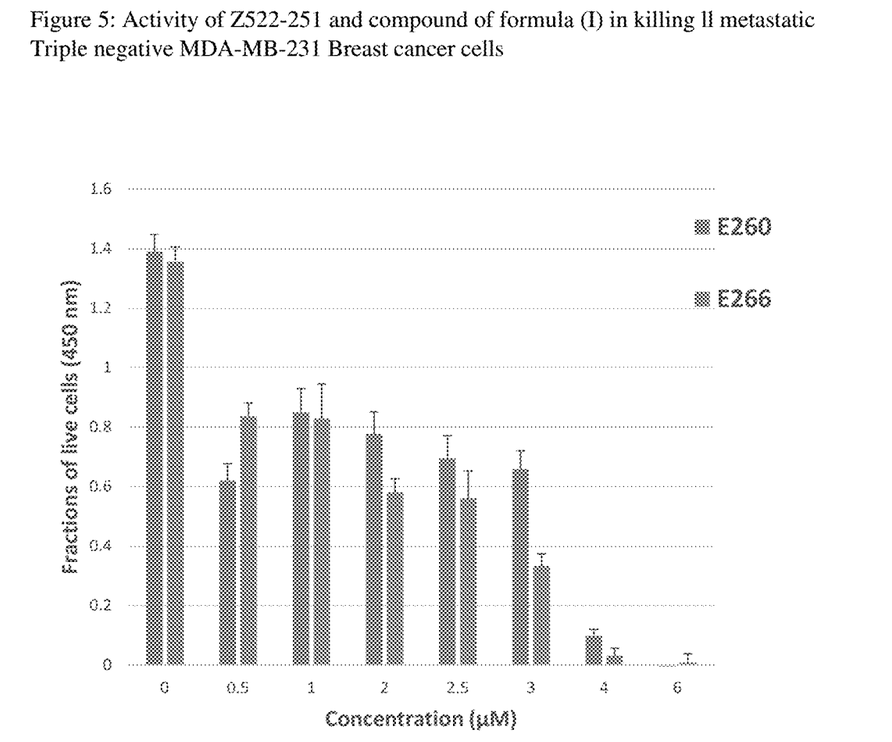
FIG. 5 shows the comparisons of the effect of compound of formula (I) (E266) and of compound Z522-251 (E260) on killing metastatic Triple negative MDA-MB-231 Breast cancer cells.
Figure 6:
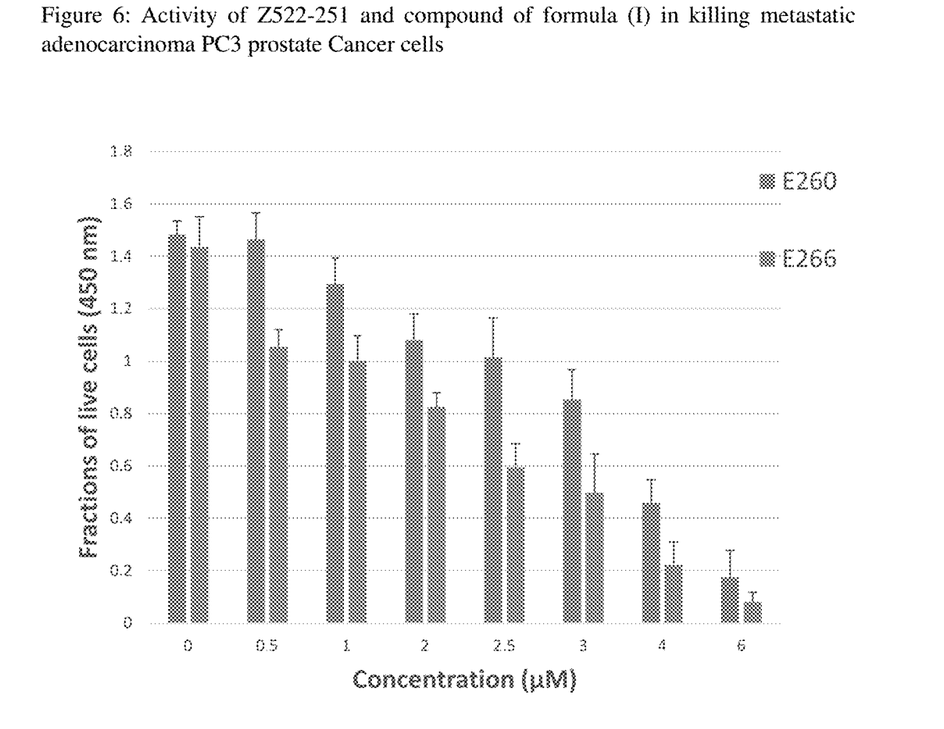
FIG. 6 shows the comparisons of the effect of compound of formula (I) (E266) and of compound Z522-251 (E260) on killing metastatic adenocarcinoma PC3 prostate Cancer cells.

FIGS. 3-6 demonstrate the comparison of the activity of both the compound of formula (I) (E266) of the present application and compound Z522-251 (E260) showing comparable results on four different cancerous cell lines, thus demonstrating its effect and efficacy in controlling cancer. FIG. 3 demonstrates a comparable activity in on killing metastatic colon cancer SW620 cells. FIG. 4 demonstrates a comparable activity on killing metastatic pancreatic ductal adenocarcinoma Su.86.86 cancer cells. FIG. 5 demonstrates a comparable activity on killing metastatic Triple negative MDA-MB-231 Breast cancer cells. FIG. 6 demonstrates a comparable activity on killing metastatic adenocarcinoma PC3 prostate Cancer cells.

Example 5

In vivo activity of the E266 (compound (I) of the present application) compared to that of the E260 (EP 2401283) in H358 derived xenografts in immune-compromised (Nude) mice.

Figure 7:
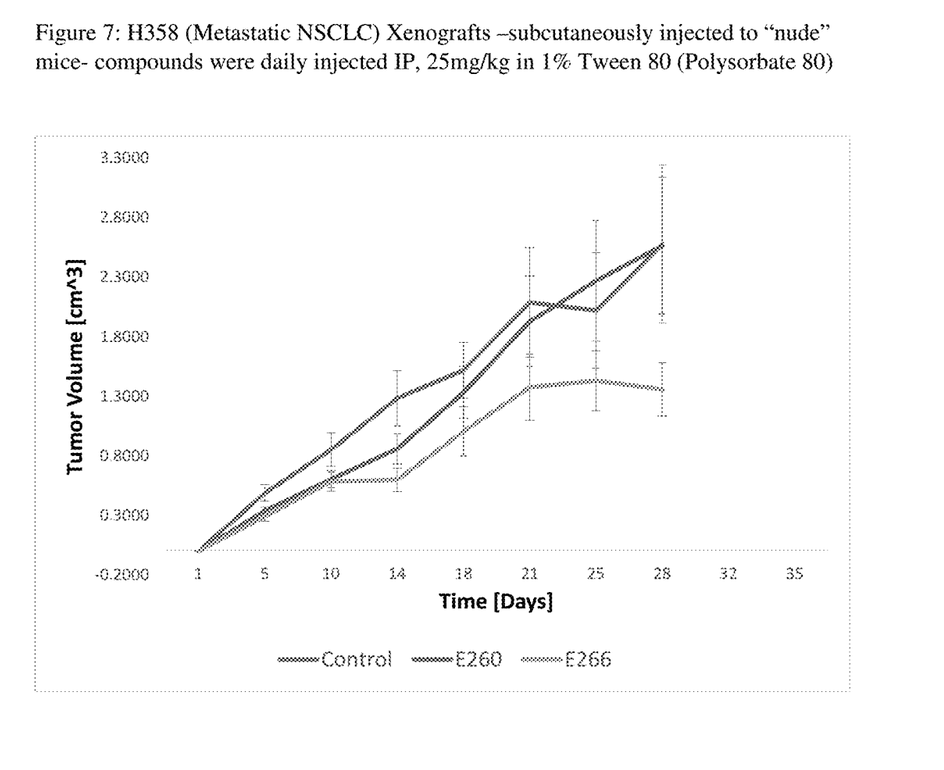
FIG. 7 shows a comparative study of in vivo activity of compound of formula (I) (E266) and of compound Z522-251 (E260) in Metastatic NSCLC) Xenografts in Nude mice.

In order to compare the relative efficacy of E266 and E260 in inhibiting the development and progression of malignant tumors in-vivo, the activity in xenograft model in mice was examined for both compounds. H358 derived xenografts in immune-compromised were elicited in (Nude) mice. The H358 cells, which are metastatic bronchioloalveolar carcinoma (BAC)-non-small cell lung cancer (NSCLC) cells, were subcutaneously injected to the back of the nude mice. When the developing xenografts reached 100 mm³ size, the inflicted animals were divided into three groups, 10 mice in each group. One group received daily intraperitoneal injection of the solvent 1% Tween 80. This solvent/emulsifier is biocompatible and is approved for pharmaceutical applications in humans. The second group received daily intraperitoneal injection of 25 mg/kg E260 dissolved in 1% Tween 80, and the third group got daily intraperitoneal injection of 25 mg/kg, E266 dissolved in the 1% Tween 80, solvent. The progression of the elicited xenografts was monitored by measuring twice a week the volumes of the developing tumors. FIG. 7 clearly demonstrates that while the E266 compound (compound (I)) managed to halt the progression of the developing tumors, E260 failed to do so. Hence E266 is superior to E260 in inhibiting the growth of in-vivo developing BAC-NSCLC, xenografts-tumors.

Example 6

In the same manner as in example 1, for comparing the activity of E260 and E266, Xenografts derived from Pancreatic ductal-adenocarcinoma cancer (PDAC), human cell-lines are examined.

Example 7

In the same manner as in example 1, for comparing the activity of E260 and E266, patients derived PDAC xenografts are examined.

Example 8

In the same manner as in example 1, for comparing the activity of E260 and E266, Xenografts derived from colorectal cancer, human cell-lines are examined.

Example 9

In the same manner as in example 1, for comparing the activity of E260 and E266, patients derived colorectal cancers xenografts are examined.

The invention claimed is:

1. A compound of formula (I) or pharmaceutical acceptable salts thereof:

2. The compound of formula (I) or the pharmaceutical acceptable salts thereof of claim 1, for use as a medicament.

3. The compound of formula (I) or the pharmaceutical acceptable salts thereof of claim 1, for use in treating cancer wherein the cancer is selected from the group consisting of colon, pancreatic, lung, and breast cancers.

4. A pharmaceutical composition comprising the compound of formula (I) or the pharmaceutical acceptable salts thereof of claim 1, together with suitable excipients.

5. The pharmaceutical composition of claim 4 for use in treating cancer wherein the cancer is selected from the group consisting of colon, pancreatic, lung, and breast cancers.

* * * * *